(12) United States Patent
Grosjean-Cournoyer et al.

(10) Patent No.: US 10,123,536 B2
(45) Date of Patent: Nov. 13, 2018

(54) FUNGICIDAL COMPOSITION COMPRISING A PYRIDYLETHYLBENZAMIDE DERIVATIVE AND A COMPOUND CAPABLE OF INHIBITING THE ERGOSTEROL BIOSYNTHESIS

(71) Applicant: BAYER INTELLECTUAL PROPERTY GMBH, Monheim (DE)

(72) Inventors: Marie-Claire Grosjean-Cournoyer, Curis au Mont d'Or (FR); Jean-Marie Gouot, St Cyr au Mont d'Or (FR)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 15/232,677

(22) Filed: Aug. 9, 2016

(65) Prior Publication Data

US 2016/0345579 A1    Dec. 1, 2016

Related U.S. Application Data

(63) Continuation of application No. 13/430,477, filed on Mar. 26, 2012, now Pat. No. 9,433,213, which is a continuation of application No. 10/587,801, filed as application No. PCT/EP2005/002568 on Feb. 10, 2005, now Pat. No. 8,168,660.

(60) Provisional application No. 60/636,956, filed on Dec. 17, 2004.

(30) Foreign Application Priority Data

Feb. 12, 2004   (EP) .................................... 04356014

(51) Int. Cl.
| | | |
|---|---|---|
| A01N 43/40 | (2006.01) | |
| A01N 37/24 | (2006.01) | |
| A01N 43/84 | (2006.01) | |
| A01N 43/30 | (2006.01) | |
| A01N 43/50 | (2006.01) | |
| A01N 43/60 | (2006.01) | |
| A01N 43/653 | (2006.01) | |

(52) U.S. Cl.
CPC ............. *A01N 43/40* (2013.01); *A01N 37/24* (2013.01); *A01N 43/30* (2013.01); *A01N 43/50* (2013.01); *A01N 43/60* (2013.01); *A01N 43/653* (2013.01); *A01N 43/84* (2013.01)

(58) Field of Classification Search
CPC combination set(s) only.
See application file for complete search history.

(56) References Cited

U.S. PATENT DOCUMENTS

| | | | |
|---|---|---|---|
| 4,723,984 A | 2/1988 | Holmwood et al. | 504/272 |
| 5,789,430 A * | 8/1998 | Jautelat | C07D 249/12 514/384 |
| 6,746,988 B2 | 6/2004 | Hopkinson et al. | 504/127 |
| 6,821,992 B1 | 11/2004 | Cooke et al. | 514/336 |
| 7,572,818 B2 | 8/2009 | Mansfield et al. | 514/357 |
| 7,776,892 B2 | 8/2010 | Grosjean-Cournoyer et al. | 514/344 |
| 7,786,148 B2 | 8/2010 | Gouot et al. | 514/344 |
| 8,168,660 B2 | 5/2012 | Grosjean-Cournoyer et al. | 514/357 |
| 8,168,860 B2 | 5/2012 | Grosjean-Cournoyer et al. | 514/357 |
| 8,410,020 B2 | 4/2013 | Gouot et al. | 504/100 |
| 9,433,213 B2 | 9/2016 | Grosjean-Cournoyer et al. | 514/357 |
| 2005/0101639 A1* | 5/2005 | Ammermann | A01N 43/653 514/345 |

FOREIGN PATENT DOCUMENTS

| | | |
|---|---|---|
| WO | WO 01/11965 A | 2/2001 |
| WO | WO 2004/016088 | 8/2003 |

OTHER PUBLICATIONS

Leonard, P.K., "Resistance risk evaluation, A European regulatory perspective," Crop Protection, vol. 19, pp. 905-909 (2000).*
International Search Report dated May 25, 2005 in corresponding International Application No. PCT/EP2005/002568.
Colby, S.R., "Calculating Synergistic and Antagonistic Responses of Herbicide Combinations," Weeds, (1967), 15, pp. 20-22.
Issac, S., "What is the mode of action of fungicides and how do fungi develop resistance?", Mycologist, vol. 13, Part 1, pp. 38-39 (Feb. 1999).

* cited by examiner

Primary Examiner — John Pak
(74) Attorney, Agent, or Firm — McBee Moore Woodward & Vanik IP, LLC

(57) ABSTRACT

A composition comprising at least a pyridylethylbenzamide derivative of general formula (I) (a) and a compound capable of inhibiting the ergosterol biosynthesis (b) in a (a)/(b) weight ratio of from 0.01 to 20.
A composition further comprising an additional fungicidal compound.

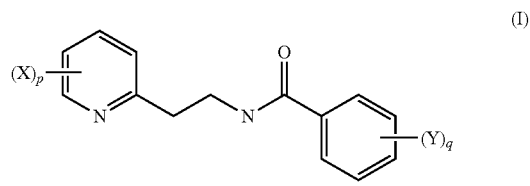

(I)

10 Claims, No Drawings

FUNGICIDAL COMPOSITION COMPRISING A PYRIDYLETHYLBENZAMIDE DERIVATIVE AND A COMPOUND CAPABLE OF INHIBITING THE ERGOSTEROL BIOSYNTHESIS

CROSS-REFERENCE TO RELATED APPLICATION(S)

The present application is a continuation of U.S. application Ser. No. 13/430,477 filed on Mar. 26, 2012, which is a continuation of U.S. application Ser. No. 10/587,801 filed on Jul. 31, 2006, now U.S. Pat. No. 8,160,660 B2 issued on May 1, 2012, which is a 35 U.S.C. § 371 national phase conversion of PCT/EP2005/002568 filed on Feb. 10, 2005, which claims priority of European Application No. 04356014.3 filed on Feb. 12, 2004 and U.S. Provisional Application No. 60/636,956 filed on Dec. 17, 2004. Applicants claim priority to each of the foregoing patent applications. The PCT International Application was published in the English language.

FIELD OF THE INVENTION

The present invention relates to novel fungicide compositions comprising a pyridylethylbenzamide derivative and a compound capable of inhibiting the ergosterol biosynthesis. The present invention also relates to a method of combating or controlling phytopathogenic fungi by applying at a locus infested or liable to be infested such a composition.

BACKGROUND OF THE INVENTION

International patent application WO 01/11965 generically discloses numerous pyridylethylbenzamide derivatives. The possibility of combining one or more of these numerous pyridylethylbenzamide derivatives with known fungicidal products to develop a fungicidal activity is disclosed in general terms, without any specific example or biological data.

It is always of high-interest in agriculture to use novel pesticidal mixtures showing a synergistic effect in order notably to avoid or to control the development of resistant strains to the active ingredients or to the mixtures of known active ingredients used by the farmer while minimising the doses of chemical products spread in the environment and reducing the cost of the treatment.

We have now found some novel fungicidal compositions which possess the above mentioned characteristics.

SUMMARY OF THE INVENTION

Accordingly, the present invention relates to a composition comprising:
a) a pyridylethylbenzamide derivative of general formula (I)

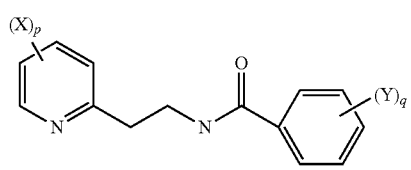

(I)

in which:
p is an integer equal to 1, 2, 3 or 4;
q is an integer equal to 1, 2, 3, 4 or 5;
each substituent X is chosen, independently of the others, as being halogen, alkyl or haloalkyl;
each substituent Y is chosen, independently of the others, as being halogen, alkyl, alkenyl, alkynyl, haloalkyl, alkoxy, amino, phenoxy, alkylthio, dialkylamino, acyl, cyano, ester, hydroxy, aminoalkyl, benzyl, haloalkoxy, halosulphonyl, halothioalkyl, alkoxyalkenyl, alkylsulphonamide, nitro, alkylsulphonyl, phenylsulphonyl or benzylsulphonyl;
as to the N-oxides of 2-pyridine thereof;
and
b) a compound capable of inhibiting the ergosterol biosynthesis;
in a (a)/(b) weight ratio of from 0.01 to 20.

DETAILED DESCRIPTION OF THE INVENTION

In the context of the present invention:
halogen means chlorine, bromine, iodine or fluorine;
each of the alkyl or acyl radicals present in the molecule contains from 1 to 10 carbon atoms, preferably from 1 to 7 carbon atoms, more preferably from 1 to 5 carbon atoms, and may be linear or branched;
each of the alkenyl or alkynyl radicals present in the molecule contains from 2 to 10 carbon atoms, preferably from 2 to 7 carbon atoms, more preferably from 2 to 5 carbon atoms, and may be linear or branched.

The composition according to the present invention provides a synergistic effect. This synergistic effect allows a reduction of the chemical substances spread into the environment and a reduction of the cost of the fungal treatment.

In the context of the present invention, the term "synergistic effect" is defined by Colby according to the article entitled "Calculation of the synergistic and antagonistic responses of herbicide combinations" Weeds, (1967), 15, pages 20-22.

The latter article mentions the formula:

$$E = x + y - \frac{x*y}{100}$$

in which E represents the expected percentage of inhibition of the disease for the combination of the two fungicides at defined doses (for example equal to x and y respectively), x is the percentage of inhibition observed for the disease by the compound (I) at a defined dose (equal to x), y is the percentage of inhibition observed for the disease by the compound (II) at a defined dose (equal to y). When the percentage of inhibition observed for the combination is greater than E, there is a synergistic effect.

The composition according to the present invention comprises a pyridylethylbenzamide derivative of general formula (I). Preferably, the present invention relates to a composition comprising a pyridylethylbenzamide derivative of general formula (I) in which the different characteristics may be chosen alone or in combination as being:
as regards p, p is 2;
as regards q, q is 1 or 2. More preferably, q is 2;
as regards X, X is chosen, independently of the others, as being halogen or haloalkyl. More preferably, X is chosen, independently of the others, as being a chloro atom or a trifluoromethyl group;
as regards Y, Y is chosen, independently of the others, as being halogen or haloalkyl. More preferably, Y is chosen, independently of the others, as being a chloro atom or a trifluoromethyl group;

More preferably, the pyridylethylbenzamide derivative of general formula (I) present in the composition of the present invention is:

N-{2-[3-chloro-5-(trifluoromethyl)-2-pyridinyl]ethyl}-2-trifluoromethylbenzamide (compound 1);

N-{2-[3-chloro-5-(trifluoromethyl)-2-pyridinyl]ethyl}-2-iodobenzamide (compound 2); or N-{2-[3,5-dichloro-2-pyridinyl]ethyl}-2-trifluoromethylbenzamide (compound 3).

Even more preferably, the pyridylethylbenzamide derivative of general formula (I) present in the composition of the present invention is N-{2-[3-chloro-5-(trifluoromethyl)-2-pyridinyl]ethyl}-2-trifluoromethylbenzamide (compound 1).

The composition according to the present invention comprises a compound capable of inhibiting the ergosterol biosynthesis. Preferably, the present invention relates to a composition comprising a compound capable of inhibiting the ergosterol biosynthesis selected from triazole derivatives, imidazole derivatives, morpholine derivatives, piperidine derivatives, fenhexamid, spiroxamine or triforine. Spiroxamine, triforine and fenhexamid are preferred.

Triazole derivatives are also preferred. According to the present invention, triazole derivatives may for example be azaconazole, bitertanol, bromuconazole, cyproconazole, difenoconazole, diniconazole, epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole, diclobutrazole, etaconazole, fluotrimazole, furconazole, furconazole-cis, triamiphos, triazbutil. Cyproconazole, fluquinconazole, prothioconazole and tebuconazole are still preferred.

Imidazole derivatives are also preferred. According to the present invention, imidazole derivatives may for example be imazalil, prochloraz, oxpoconazole fumarate, pefurazoate or triflumizole. Prochloraz is still preferred.

Morpholine derivatives are also preferred. According to the present invention, morpholine derivatives may for example be aldimorph, dodemorph, fenpropimorph or tridemorph. Fenpropimorph and tridemorph are still preferred.

Piperidine derivatives are also preferred. According to the present invention, piperidine derivatives may for example be fenpropidin or piperalin.

The composition according to the present invention comprises at least a pyridylethylbenzamide derivative of general formula (I) (a) and a compound capable of inhibiting the ergosterol biosynthesis (b) in an (a)/(b) weight ratio of from 0.01 to 20; preferably of from 0.05 to 10; even more preferably, of from 0.1 to 5.

The composition of the present invention may further comprise at least one other different fungicide active ingredient (c).

The fungicidal active ingredient (c) may be selected from azaconazole, azoxystrobin, (Z)—N-[α-(cyclopropylmethoxyimino)-2,3-difluoro-6-(trifluoromethyl)benzyl]-2-phenylacetamide, 6-iodo-2-propoxy-3-propylquinazolin-4 (3M-one, benalaxyl, benomyl, benthiavalicarb, biphenyl, bitertanol, blasticidin-S, boscalid, borax, bromuconazole, bupirimate, sec-butylamine, calcium polysulfide, captafol, captan, carbendazim, carboxin, carpropamid, chinomethionat, chlorothalonil, chlozolinate, copper hydroxide, copper octanoate, copper oxychloride, copper sulfate, cuprous oxide, cyazofamid, cymoxanil, cyproconazole, cyprodinil, dazomet, debacarb, dichlofluanid, dichlorophen, diclobutrazole, diclocymet, diclomezine, dicloran, diethofencarb, difenoconazole, difenzoquat metilsulfate, difenzoquat, diflumetorim, dimethirimol, dimethomorph, diniconazole, dinobuton, dinocap, diphenylamine, dithianon, dodemorph, dodemorph acetate, dodine, edifenphos, epoxiconazole, etaconazole, ethaboxam, ethirimol, ethoxyquin, etridiazole, famoxadone, fenamidone, fenarimol, fenbuconazole, fenfuram, fenhexamid, fenpiclonil, fenoxanil, fenpropidin, fenpropimorph, fentin, fentin hydroxide, fentin acetate, ferbam, ferimzone, fluazinam, fludioxonil, fluoroimide, fluoxastrobin, fluquinconazole, flusilazole, flusulfamide, flutolanil, flutriafol, folpet, formaldehyde, fosetyl, fosetyl-aluminium, fuberidazole, furalaxyl, furametpyr, guazatine, guazatine acetates, hexachlorobenzene, hexaconazole, 8-hydroxyquinoline sulfate, potassium hydroxyquinoline sulfate, hymexazol, imazalil sulfate, imazalil, imibenconazole, iminoctadine, iminoctadine triacetate, ipconazole, iprobenfos, iprodione, iprovalicarb, isoprothiolane, kasugamycin, kasugamycin hydrochloride hydrate, kresoxim-methyl, mancopper, mancozeb, maneb, mepanipyrim, mepronil, mercuric chloride, mercuric oxide, mercurous chloride, metalaxyl, metalaxyl-M, metam-sodium, metam, metconazole, methasulfocarb, methyl isothiocyanate, metiram, metominostrobin, mildiomycin, myclobutanil, nabam, nickel bis(dimethyldithiocarbamate), nitrothal-isopropyl, nuarimol, octhilinone, ofurace, oleic acid, oxadixyl, oxinecopper, oxpoconazole fumarate, oxycarboxin, pefurazoate, penconazole, pencycuron, pentachlorophenol, sodium pentachlorophenoxide, pentachlorophenyl laurate, phenylmercury acetate, sodium 2-phenylphenoxide, 2-phenylphenol, phosphorous acid, phthalide, picoxystrobin, piperalin, polyoxinspolyoxin B, polyoxin, polyoxorim, probenazole, prochloraz, procymidone, propamocarb hydrochloride, propamocarb, propiconazole, propineb, prothioconazole, pyraclostrobin, pyrazophos, pyributicarb, pyrifenox, pyrimethanil, pyroquilon, quinoxyfen, quintozene, silthiofam, simeconazole, spiroxamine, sulfur, tar oils, tebuconazole, tecnazene, tetraconazole, thiabendazole, thifluzamide, thiophanate-methyl, thiram, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram and zoxamide.

Preferably, fungicidal active ingredient (c) is selected from trifloxystrobin, fluoxastrobin, pyrimethanil, thiabendazole, guazatine, imidoctadine, picoxystrobin, pyraclostrobin, azoxystrobin, dimoxystrobin, metaminostrobin, 2-{2-[6-(3-chloro-2-methylphenoxy)-5-fluoro-pyrimidin-4-yloxy]-phenyl}2-methoxyimino-N-methylacetamide, captane, dodine, propineb, mancozeb, spiroxamine, prothioconazole, tebuconazole, thirame, tolylfluanid, iminoctadine, dithianon, sulphur, copper hydroxide, copper octanoate, copper oxychloride, copper sulfate, dinocap, quinoxyfen, 2-butoxy-6-iodo-3-propyl-benzopyran-4-one, fludioxonil, triazoxide, fosetyl-Al and phosphorous acid.

Where the third active ingredient (c) as defined above is present in the composition, this compound may be present in an amount of (a):(b):(c) weight ratio of from 1:0.01:0.01 to 1:20:20; the ratios of compound (a) and compound (c) varying independently from each other. Preferably, the (a):(b):(c) weight ratio may be of from 1:0.05:0.05 to 1:10:10.

Following compositions may be cited to illustrate in a non-limited manner the present invention: compound 1 with fenhexamid, compound 1 with spiroxamine, compound 1 with triforine, compound 1 with azaconazole, compound 1 with bitertanol, compound 1 with bromuconazole, compound 1 with cyproconazole, compound 1 with difenoconazole, compound 1 with diniconazole, compound 1 with epoxiconazole, compound 1 with fenbuconazole, compound 1 with fluquinconazole, compound 1 with flusilazole, compound 1 with flutriafol, compound 1 with hexaconazole, compound 1 with imibenconazole, compound 1 with ipconazole, compound 1 with metconazole, compound 1 with myclobutanil, compound 1 with penconazole, compound 1 with propiconazole, compound 1 with prothioconazole, compound 1 with simeconazole, compound 1 with tebuconazole, compound 1 with tetraconazole, compound 1 with triadimefon, compound 1 with triadimenol, compound 1 with triticonazole, compound 1 with diclobutrazole, compound 1 with etaconazole, compound 1 with fluotrimazole, compound 1 with furconazole, compound 1 with furconazole-cis, compound 1 with triamiphos, compound 1 with triazbutil, compound 1 with imazalil, compound 1 with prochloraz, compound 1 with oxpoconazole fumarate, compound 1 with pefurazoate, compound 1 with triflumizole, compound 1 with aldimorph, compound 1 with dodemorph, compound 1 with fenpropimorph, compound 1 with tridemorph, compound 1 with fenpropidin, compound 1 with piperalin, compound 2 with fenhexamid, compound 2 with spiroxamine, compound 2 with triforine, compound 2 with azaconazole, compound 2 with bitertanol, compound 2 with bromuconazole, compound 2 with cyproconazole, compound 2 with difenoconazole, compound 2 with diniconazole, compound 2 with epoxiconazole, compound 2 with fenbuconazole, compound 2 with fluquinconazole, compound 2 with flusilazole, compound 2 with flutriafol, compound 2 with hexaconazole, compound 2 with imibenconazole, compound 2 with ipconazole, compound 2 with metconazole, compound 2 with myclobutanil, compound 2 with penconazole, compound 2 with propiconazole, compound 2 with prothioconazole, compound 2 with simeconazole, compound 2 with tebuconazole, compound 2 with tetraconazole, compound 2 with triadimefon, compound 2 with triadimenol, compound 2 with triticonazole, compound 2 with diclobutrazole, compound 2 with etaconazole, compound 2 with fluotrimazole, compound 2 with furconazole, compound 2 with furconazole-cis, compound 2 with triamiphos, compound 2 with triazbutil, compound 2 with imazalil, compound 2 with prochloraz, compound 2 with oxpoconazole fumarate, compound 2 with pefurazoate, compound 2 with triflumizole, compound 2 with aldimorph, compound 2 with dodemorph, compound 2 with fenpropimorph, compound 2 with tridemorph, compound 2 with fenpropidin, compound 2 with piperalin, compound 3 with fenhexamid, compound 3 with spiroxamine, compound 3 with triforine, compound 3 with azaconazole, compound 3 with bitertanol, compound 3 with bromuconazole, compound 3 with cyproconazole, compound 3 with difenoconazole, compound 3 with diniconazole, compound 3 with epoxiconazole, compound 3 with fenbuconazole, compound 3 with fluquinconazole, compound 3 with flusilazole, compound 3 with flutriafol, compound 3 with hexaconazole, compound 3 with imibenconazole, compound 3 with ipconazole, compound 3 with metconazole, compound 3 with myclobutanil, compound 3 with penconazole, compound 3 with propiconazole, compound 3 with prothioconazole, compound 3 with simeconazole, compound 3 with tebuconazole, compound 3 with tetraconazole, compound 3 with triadimefon, compound 3 with triadimenol, compound 3 with triticonazole, compound 3 with diclobutrazole, compound 3 with etaconazole, compound 3 with fluotrimazole, compound 3 with furconazole, compound 3 with furconazole-cis, compound 3 with triamiphos, compound 3 with triazbutil, compound 3 with imazalil, compound 3 with prochloraz, compound 3 with oxpoconazole fumarate, compound 3 with pefurazoate, compound 3 with triflumizole, compound 3 with aldimorph, compound 3 with dodemorph, compound 3 with fenpropimorph, compound 3 with tridemorph, compound 3 with fenpropidin, compound 3 with piperalin.

The composition according to the present invention may further comprise an other additional component such as an agriculturally acceptable support, carrier or filler.

In the present specification, the term "support" denotes a natural or synthetic, organic or inorganic material with which the active material is combined to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise other additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be comprised between 5% and 40% by weight of the composition.

Additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention may contain from 0.05 to 99% (by weight) of active material, preferably 10 to 70% by weight.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before they are applied to the crop.

The fungicidal compositions of the present invention can be used to curatively or preventively control phytopathogenic fungi of crops. Thus, according to a further aspect of the present invention, there is provided a method for preventively or curatively controlling phytopathogenic fungi of crops characterised in that a fungicidal composition as hereinbefore defined is applied to the seed, the plant and/or to the fruit of the plant or to the soil in which the plant is growing or in which it is desired to grow.

The composition as used against phytopathogenic fungi of crops comprises an effective and non-phytotoxic amount of an active material of general formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be combated or controlled, the type of crop, the climatic conditions and the compounds included in the fungicidal composition according to the invention.

This amount can be determined by systematic field trials, which are within the capabilities of a person skilled in the art.

The method of treatment according to the present invention is useful to treat propagation material such as tubers or rhizomes, but also seeds, seedlings or seedlings, pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Among the plants that can be protected by the method according to the invention, mention may be made of cotton; flax; vine; fruit crops such as *Rosaceae* sp. (for instance pip fruits such as apples and pears, but also stone fruits such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruits); leguminous crops such as *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); big crops such as *Graminae* sp. (for instance maize, cereals such as wheat, rice, barley and triticale), *Asteraceae* sp. (for instance sunflower), *Cruciferae* sp. (for instance colza), *Papilionaceae* sp. (for instance soja), *Solanaceae* sp. (for instance potatoes), *Chenopodiaceae* sp. (for instance beetroots); horticultural and forest crops; as well as genetically modified homologues of these crops.

Among the plants and the possible diseases of these plants protected by the method according to the present invention, mention may be made of:
  wheat, as regards controlling the following seed diseases: fusaria (*Microdochium nivale* and *Fusarium roseum*), stinking smut (*Tilletia caries, Tilletia controversa* or *Tilletia indica*), septoria disease (*Septoria nodorum*) and loose smut;
  wheat, as regards controlling the following diseases of the aerial parts of the plant: cereal eyespot (*Tapesia yallundae, Tapesia acuiformis*), take-all (*Gaeumannomyces graminis*), foot blight (*F. culmorum, F. graminearum*), black speck (*Rhizoctonia cerealis*), powdery mildew (*Erysiphe graminis* forma specie *tritici*), rusts (*Puccinia striiformis* and *Puccinia recondita*) and septoria diseases (*Septoria tritici* and *Septoria nodorum*);
  wheat and barley, as regards controlling bacterial and viral diseases, for example barley yellow mosaic;
  barley, as regards controlling the following seed diseases: net blotch (*Pyrenophora graminea, Pyrenophora teres* and *Cochliobolus sativus*), loose smut (*Ustilago nuda*) and fusaria (*Microdochium nivale* and *Fusarium roseum*);
  barley, as regards controlling the following diseases of the aerial parts of the plant: cereal eyespot (*Tapesia yallundae*), net blotch (*Pyrenophora teres* and *Cochliobolus sativus*), powdery mildew (*Erysiphe graminis* forma specie *hordei*), dwarf leaf rust (*Puccinia hordei*) and leaf blotch (*Rhynchosporium secalis*);
  potato, as regards controlling tuber diseases (in particular *Helminthosporium solani, Phoma tuberosa, Rhizoctonia solani, Fusarium solani*), mildew (*Phytopthora infestans*) and certain viruses (virus Y);
  potato, as regards controlling the following foliage diseases: early blight (*Alternaria solani*), mildew (*Phytophthora infestans*);
  cotton, as regards controlling the following diseases of young plants grown from seeds: damping-off and collar rot (*Rhizoctonia solani, Fusarium oxysporum*) and black root rot (*Thielaviopsis basicola*);
  protein yielding crops, for example peas, as regards controlling the following seed diseases: anthracnose (*Ascochyta pisi, Mycosphaerella pinodes*), fusaria (*Fusarium oxysporum*), grey mould (*Botrytis cinerea*) and mildew (*Peronospora pisi*);
  oil-bearing crops, for example rape, as regards controlling the following seed diseases: *Phoma lingam, Alternaria brassicae* and *Sclerotinia sclerotiorum;*
  corn, as regards controlling seed diseases: (*Rhizopus* sp., *Penicillium* sp., *Trichoderma* sp., *Aspergillus* sp., and *Gibberella fujikuroi*);
  flax, as regards controlling the seed disease: *Alternaria linicola;*
  forest trees, as regards controlling damping-off (*Fusarium oxysporum, Rhizoctonia solani*);
  rice, as regards controlling the following diseases of the aerial parts: blast disease (*Magnaporthe grisea*), bordered sheath spot (*Rhizoctonia solani*);
  leguminous crops, as regards controlling the following diseases of seeds or of young plants grown from seeds: damping-off and collar rot (*Fusarium oxysporum, Fusarium roseum, Rhizoctonia solani, Pythium* sp.);
  leguminous crops, as regards controlling the following diseases of the aerial parts: grey mould (*Botrytis* sp.), powdery mildews (in particular *Erysiphe cichoracearum, Sphaerotheca fuliginea* and *Leveillula taurica*), fusaria (*Fusarium oxysporum, Fusarium roseum*), leaf spot (*Cladosporium* sp.), alternaria leaf spot (*Alternaria* sp.), anthracnose (*Colletotrichum* sp.), septoria leaf spot (*Septoria* sp.), black speck (*Rhizoctonia solani*), mildews (for example *Bremia lactucae, Peronospora* sp., *Pseudoperonospora* sp., *Phytophthora* sp.);

fruit trees, as regards diseases of the aerial parts: *monilia* disease (*Monilia fructigenae, M. laxa*), scab (*Venturia inaequalis*), powdery mildew (*Podosphaera leucotricha*);

vine, as regards diseases of the foliage: in particular grey mould (*Botrytis cinerea*), powdery mildew (*Uncinula necator*), black rot (*Guignardia biwelli*) and mildew (*Plasmopara viticola*);

beetroot, as regards the following diseases of the aerial parts: *cercospora* blight (*Cercospora beticola*), powdery mildew (*Erysiphe beticola*), leaf spot (*Ramularia beticola*).

The fungicidal composition according to the present invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

The fungicidal composition according to the present invention may also be used in the treatment of genetically modified organisms with the compounds according to the invention or the agrochemical compositions according to the invention. Genetically modified plants are plants into in which genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

The dose of active material usually applied in the treatment according to the present invention is generally and advantageously between 10 and 2000 g/ha, preferably between 20 and 1500 g/ha for applications in foliar treatment. The dose of active substance applied is generally and advantageously between 1 and 200 g per 100 kg of seed, preferably between 2 and 150 g per 100 kg of seed in the case of seed treatment. It is clearly understood that the doses indicated above are given as illustrative examples of the invention. A person skilled in the art will know how to adapt the application doses according to the nature of the crop to be treated.

The compositions according to the present invention may also be used fore the preparation of composition useful to curatively or preventively treat human and animal fungal diseases such as, for example, mycoses, dermatoses, *trichophyton* diseases and candidiases or diseases caused by *Aspergillus* spp. or *Candida* spp., for example *Aspergillus fumigatus* or *Candida albicans* respectively.

The present invention will now be illustrated with the following example:

Example 1: Efficacy Against *Mycosphaerella graminicola* of a Mixture Containing N-{2-[3-chloro-5-(trifluoro methyl)-2-pyridinyl]ethyl}-2-trifluoromethylbenzamide (Compound 1) and tebuconazole The active ingredients tested are prepared by potter homogenisation in a mixture of acetone/tween/water. This suspension is then diluted with water to obtain the desired active material concentration.

Wheat plants (Scipion variety), sown on a 50/50 peat soil-pozzolana substrate in starter cups and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Mycosphaerella graminicola* spores (500 000 spores per ml). The spores are collected from a 7-day-old culture. The contaminated wheat plants are incubated for 72 hours at 18° C. and at 100% relative humidity, and then for 21 to 28 days at 90% relative humidity.

Grading (% of efficacy) is carried out 21 to 28 days after the contamination, in comparison with the control plants.

The following table summarises the results obtained when tested compound 1 and tebuconazole alone and in a 1/1 weight ratio mixture.

|  | Dose (g/ha) | % Efficacy | Synergism (Colby) |
| --- | --- | --- | --- |
| Compound 1 | 15 | 25 | — |
|  | 31 | 65 | — |
| Tebuconazole | 15 | 15 | — |
|  | 31 | 15 | — |
| Compound 1 + tebuconazole | 15 + 15 | 75 | +39 |
| (Ratio 1/1) | 31 + 31 | 80 | +10 |

According to the Colby method, a synergistic effect of the mixtures tested has been observed.

Example 2: Efficacy Against *Erysiphe graminis* f. Sp. *Graminis* of a Mixture Containing N-{2-[3-chloro-5-(trifluoromethyl)-2-pyridinyl]ethyl}-2-trifluoromethylbenzamide (Compound 1) and prothioconazole The active ingredients tested are prepared by potter homogenisation in a mixture of acetone/tween/water. This suspension is then diluted with water to obtain the desired active material concentration.

Wheat plants (Audace variety) in starter cups, sown on 50/50 peat soil-pozzolana substrate and grown at 12° C., are treated at the 1-leaf stage (10 cm tall) by spraying with the aqueous suspension described above.

Plants, used as controls, are treated with an aqueous solution not containing the active material.

After 24 hours, the plants are contaminated by dusting them with *Erysiphe graminis* f. sp. *tritici* spores, the dusting being carried out using diseased plants.

Grading is carried out 7 to 14 days after the contamination, in comparison with the control plants.

The following table summarises the results obtained when tested compound 1 and prothioconazole alone and in a 1/2 weight ratio mixture.

|  | Dose (g/ha) | % Efficacy | Synergism (Colby) |
| --- | --- | --- | --- |
| Compound 1 | 125 | 20 | — |
|  | 62.5 | 0 | — |
| Prothioconazole | 250 | 60 | — |
|  | 125 | 0 | — |
| Compound 1 + prothioconazole | 125 + 250 | 85 | +17 |
| (Ratio 1/2) | 62 + 125 | 70 | +70 |

According to the Colby method, a synergistic effect of the mixtures tested has been observed.

Example 3: Efficacy Against *Botrytis cinerea* of a Mixture Containing N-{2-[3-chloro-5-(trifluoromethyl)-2-pyridinyl]ethyl}-2-trifluoromethylbenzamide (Compound 1) and propiconazole The active ingredients tested are prepared by potter homogenisation in a mixture of acetone/tween/water. This suspension is then diluted with water to obtain the desired active material concentration.

Gherkin plants (Petit vert de Paris variety) in starter cups, sown on a 50/50 peat soil-pozzolana substrate and grown at 18-20° C., are treated at the cotyledon Z11 stage by spraying with the aqueous suspension described above. Plants, used as controls, are treated with an aqueous solution not containing the active material.

After 24 hours, the plants are contaminated by depositing drops of an aqueous suspension of *Botrytis cinerea* spores (150,000 spores per ml) on upper surface of the leaves. The spores are collected from a 15-day-old culture and are suspended in a nutrient solution composed of:
  20 g/L of gelatine
  50 g/L of cane sugar
  2 g/L of $NH_4NO_3$
  1 g/L of $KH_2PO_4$ The contaminated gherkin plants are settled for 5/7 days in a climatic room at 15-11° C. (day/night) and at 80% relative humidity. Grading (% of efficacy) is carried out 5 to 7 days after the contamination, in comparison with the control plants.

The following table summarises the results obtained when tested compound 1 and propiconazole alone and in different weight ratio mixtures.

|  | Dose (ppm) | % Efficacy | Synergism (Colby) |
| --- | --- | --- | --- |
| Compound 1 | 12 | 0 | — |
|  | 37 | 30 | — |
|  | 111 | 80 | — |
| Propiconazole | 37 | 30 | — |
|  | 111 | 50 | — |
|  | 333 | 70 | — |
| Compound 1 + propiconazole (Ratio 1/9) | 37 + 333 | 100 | 21 |
|  | 12 + 111 | 100 | 50 |
| Compound 1 + propiconazole (Ratio 1/3) | 37 + 111 | 100 | +35 |
| Compound 1 + propiconazole (Ratio 1/1) | 37 + 37 | 80 | +29 |

According to the Colby method, a synergistic effect of the mixtures tested has been observed.

Example 4: Efficacy Against *Erysiphe graminis* f. sp. *graminis* of a Mixture Containing N-{2-[3-chloro-5-(trifluoromethyl)-2-pyridinyl]ethyl}-2-trifluoromethylbenzamide (Compound 1) and cyproconazole The formulated (concentrated suspension) compounds are diluted with water to obtain the desired active material concentration Wheat plants (Audace variety) in starter cups, sown on 50/50 peat soil-pozzolana substrate and grown at 12° C., are treated at the 1-leaf stage (10 cm tall) by spraying with the aqueous suspension described above.

Plants, used as controls, are treated with an aqueous solution not containing the active material.

After 24 hours, the plants are contaminated by dusting them with *Erysiphe graminis* f. sp. *tritici* spores, the dusting being carried out using diseased plants.

Grading is carried out 7 to 14 days after the contamination, in comparison with the control plants.

The following table summarises the results obtained when tested compound 1 and cyproconazole alone and in a 2/1 weight ratio mixture.

|  | Dose (g/ha) | % Efficacy | Synergism (Colby) |
| --- | --- | --- | --- |
| Compound 1 | 62.5 | 10 | — |
| Cyproconazole | 31.2 | 15 | — |
| Compound 1 + cyproconazole (Ratio 2/1) | 62.5 + 31.2 | 60 | +37 |

According to the Colby method, a synergistic effect of the mixtures tested has been observed.

Example 5: Efficacy Against *Botrytis cinerea* of a Mixture Containing N-{2-[3-chloro-5-(trifluoromethyl)-2-pyridinyl]ethyl}-2-trifluoromethylbenzamide Compound 1) and difenconazole The active ingredients tested are prepared by potter homogenisation in a mixture of acetone/tween/water. This suspension is then diluted with water to obtain the desired active material concentration.

Gherkin plants (Petit vert de Paris variety) in starter cups, sown on a 50/50 peat soil-pozzolana substrate and grown at 18-20° C., are treated at the cotyledon Z11 stage by spraying with the aqueous suspension described above. Plants, used as controls, are treated with an aqueous solution not containing the active material.

After 24 hours, the plants are contaminated by depositing drops of an aqueous suspension of *Botrytis cinerea* spores (150,000 spores per ml) on upper surface of the leaves. The spores are collected from a 15-day-old culture and are suspended in a nutrient solution composed of:
  20 g/L of gelatine
  50 g/L of cane sugar
  2 g/L of $NH_4NO_3$
  1 g/L of $KH_2PO_4$ The contaminated gherkin plants are settled for 5/7 days in a climatic room at 15-11° C. (day/night) and at 80% relative humidity. Grading (% of efficacy) is carried out 5 to 7 days after the contamination, in comparison with the control plants.

The following table summarises the results obtained when tested compound 1 and difenconazole alone and in different weight ratio mixtures.

|  | Dose (ppm) | % Efficacy | Synergism (Colby) |
| --- | --- | --- | --- |
| Compound 1 | 37 | 0 | — |
|  | 111 | 80 | — |
| Difenconazole | 111 | 15 | — |
|  | 333 | 25 | — |
| Compound 1 + difenconazole (Ratio 1/3) | 37 + 111 | 80 | +65 |

| | Dose (ppm) | % Efficacy | Synergism (Colby) |
|---|---|---|---|
| Compound 1 + difenconazole (Ratio 1/1) | 111 + 111 | 100 | +17 |
| Compound 1 + difenconazole (Ratio 1/9) | 111 + 333 | 80 | +55 |

According to the Colby method, a synergistic effect of the mixtures tested has been observed.

Example 6: Efficacy Against *Botrytis cinerea* of a Mixture Containing N-{2-[3-chloro-5-(trifluoromethyl)-2-pyridinyl]ethyl}-2-trifluoromethylbenzamide (Compound 1) and hexaconazole The active ingredients tested are prepared by potter homogenisation in a mixture of acetone/tween/water. This suspension is then diluted with water to obtain the desired active material concentration.

Gherkin plants (Petit vert de Paris variety) in starter cups, sown on a 50/50 peat soil-pozzolana substrate and grown at 18-20° C., are treated at the cotyledon Z11 stage by spraying with the aqueous suspension described above. Plants, used as controls, are treated with an aqueous solution not containing the active material.

After 24 hours, the plants are contaminated by depositing drops of an aqueous suspension of *Botrytis cinerea* spores (150,000 spores per ml) on upper surface of the leaves. The spores are collected from a 15-day-old culture and are suspended in a nutrient solution composed of:
20 g/L of gelatine
50 g/L of cane sugar
2 g/L of NH4NO3
1 g/L of KH2PO4

The contaminated gherkin plants are settled for 5/7 days in a climatic room at 15-11° C. (day/night) and at 80% relative humidity. Grading (% of efficacy) is carried out 5 to 7 days after the contamination, in comparison with the control plants.

The following table summarises the results obtained when tested compound 1 and hexaconazole alone and in a 1:27 weight ratio mixture.

| | Dose (ppm) | % Efficacy | Synergism (Colby) |
|---|---|---|---|
| Compound 1 | 4 | 10 | — |
| Hexaconazole | 111 | 15 | — |
| Compound 1 + hexaconazole (Ratio 1:27) | 4 + 111 | 98 | +19 |

According to the Colby method, a synergistic effect of the mixtures tested has been observed.

Example 7: Efficacy Against *Erysiphe graminis* f. sp. *graminis* of a Mixture Containing N-{2-[3-chloro-5-(trifluoromethyl)-2-pyridinyl]ethyl}-2-trifluoromethylbenzamide (Compound 1) and metconazole The formulated compounds are diluted with water to obtain the desired active material concentration. Wheat plants (Audace variety) in starter cups, sown on 50/50 peat soil-pozzolana substrate and grown at 12° C., are treated at the 1-leaf stage (10 cm tall) by spraying with the aqueous suspension described above.

Plants, used as controls, are treated with an aqueous solution not containing the active material.

After 24 hours, the plants are contaminated by dusting them with *Erysiphe graminis* f. sp. *tritici* spores, the dusting being carried out using diseased plants.

Grading is carried out 7 to 14 days after the contamination, in comparison with the control plants.

The following table summarises the results obtained when tested compound 1 and metconazole alone and in a 8:1 weight ratio mixture.

| | Dose (g/ha) | % Efficacy | Synergism (Colby) |
|---|---|---|---|
| Compound 1 | 250 | 40 | — |
| Metconazole | 31.2 | 50 | — |
| Compound 1 + metconazole (Ratio 8:1) | 250 + 31.2 | 80 | +10 |

According to the Colby method, a synergistic effect of the mixtures tested has been observed.

Example 8: Efficacy Against *Puccinia recondita* of a Mixture Containing N-{2-[3-chloro-5-(trifluoromethyl)-2-pyridinyl]ethyl}-2-trifluoromethylbenzamide (Compound 1) and epoxiconazole The formulated compounds are diluted with water to obtain the desired active material concentration Wheat plants (Scipion variety) in starter cups, sown on 50/50 peat soil-pozzolana substrate and grown at 12° C., are treated at the 1-leaf stage (10 cm tall) by spraying with the aqueous suspension described above.

Plants, used as controls, are treated with an aqueous solution not containing the active material.

After 24 hours, the plants are contaminated by spraying the leaves with an aqueous suspension of *Puccinia recondita* spores (100,000 spores per ml). The spores are collected from a 10-day-old contaminated wheat and are suspended in water containing 2.5 ml/l of tween 80 10%. The contaminated wheat plants are incubated for 24 hours at 20° C. and at 100% relative humidity, and then for 10 days at 20° C. and at 70% relative humidity. Grading is carried out 10 days after the contamination, in comparison with the control plants.

The following table summarises the results obtained when tested compound 1 and epoxiconazole alone and in different weight ratio mixtures.

| | Dose (g/ha) | % Efficacy | Synergism (Colby) |
|---|---|---|---|
| Compound 1 | 62.5 | 0 | — |
| | 250 | 0 | — |
| Epoxiconazole | 15.6 | 25 | — |
| Compound 1 + epoxiconazole (Ratio 16:1) | 250 + 15.6 | 80 | +55 |
| Compound 1 + epoxiconazole (Ratio 4:1) | 62.5 + 15.6 | 85 | +60 |

According to the Colby method, a synergistic effect of the mixtures tested has been observed Example 9: Efficacy Against *Botrytis cinerea* of a Mixture Containing N-{2-[3-chloro-5-(trifluoromethyl)-2-pyridinyl]ethyl}-2-trifluoromethylbenzamide (Compound 1) and myclobutanil The formulated compounds are diluted with water to obtain the desired active material concentration.

Gherkin plants (Petit vert de Paris variety) in starter cups, sown on a 50/50 peat soil-pozzolana substrate and grown at 18-20° C., are treated at the cotyledon Z11 stage by spraying with the aqueous suspension, described above. Plants, used as controls, are treated with an aqueous solution not containing the active material.

After 24 hours, the plants are contaminated by depositing drops of an aqueous suspension of *Botrytis cinerea* spores (150,000 spores per ml) on upper surface of the leaves. The spores are collected from a 15-day-old culture and are suspended in a nutrient solution composed of:
20 g/L of gelatine
50 g/L of cane sugar
2 g/L of NH4NO3
1 g/L of KH2PO4

The contaminated gherkin plants are settled for 5/7 days in a climatic room at 15-11° C. (day/night) and at 80% relative humidity. Grading (% of efficacy) is carried out 5 to 7 days after the contamination, in comparison with the control plants.

The following table summarises the results obtained when tested compound 1 and myclobutanil alone and in different weight ratio mixtures.

|  | Dose (ppm) | % Efficacy | Synergism (Colby) |
|---|---|---|---|
| Compound 1 | 12.3 | 0 | — |
|  | 37 | 50 | — |
| Myclobutanil | 333 | 0 | — |
| Compound 1 + myclobutanil (Ratio 1:27) | 12.3 + 333 | 53 | +53 |
| Compound 1 + myclobutanil (Ratio 1:9) | 37 + 333 | 70 | +20 |

According to the Colby method, a synergistic effect of the mixtures tested has been observed.

Example 10: Efficacy Against *Puccinia recondita* of a Mixture Containing N-{2-[3-chloro-5-(trifluoromethyl)-2-pyridinyl]ethyl}-2-trifluoromethylbenzamide (Compound 1) and triadimenol The active ingredients tested are prepared by potter homogenisation in a mixture of acetone/tween/water. This suspension is then diluted with water to obtain the desired active material concentration.

Wheat plants (Scipion variety) in starter cups, sown on 50/50 peat soil-pozzolana substrate and grown at 12° C., are treated at the 1-leaf stage (10 cm tall) by spraying with the aqueous suspension described above.

Plants, used as controls, are treated with an aqueous solution not containing the active material.

After 24 hours, the plants are contaminated by spraying the leaves with an aqueous suspension of *Puccinia recondita* spores (100,000 spores per ml). The spores are collected from a 10-day-old contaminated wheat and are suspended in water containing 2.5 ml/l of tween 80 10%. The contaminated wheat plants are incubated for 24 hours at 20° C. and at 100% relative humidity, and then for 10 days at 20° C. and at 70% relative humidity. Grading is carried out 10 days after the contamination, in comparison with the control plants.

The following table summarises the results obtained when tested compound 1 and triadimenol alone and in a 1:1 weight ratio mixture.

|  | Dose (g/ha) | % Efficacy | Synergism (Colby) |
|---|---|---|---|
| Compound 1 | 250 | 0 | — |
| Triadimenol | 250 | 50 | — |
| Compound 1 + triadimenol (Ratio 1:1) | 250 + 250 | 70 | +20 |

According to the Colby method, a synergistic effect of the mixtures tested has been observed.

Example 11: Efficacy Against *Sphaerotheca fuliginea* of a Composition Containing N-{2-[3-chloro-5-(trifluoromethyl)-2-pyridinyl]ethyl}-2-trifluoromethylbenzamide (Compound 1) and fenhexamid The formulated compounds are diluted with water to obtain the desired active material concentration Gherkin plants (Vert petit de Paris variety) in starter cups, sown on a 50/50 peat soil-pozzolana substrate and grown at 20° C./23° C., are treated at the 2-leaves stage by spraying with the aqueous suspension described above. Plants, used as controls, are treated with an aqueous solution not containing the active material.

After 24 hours, the plants are contaminated by spraying them with an aqueous suspension of Sphaerotheca *fuliginea* spores (100 000 spores per ml). The spores are collected from a contaminated plants. The contaminated gerkhin plants are incubated at about 20° C./25° C. and at 60/70% relative humidity.

Grading (% of efficacy) is carried out 21 days after the contamination, in comparison with the control plants.

The following table summarises the results obtained when tested compound 1 and fenhexamid alone and in a 1:9 weight ratio mixture.

|  | Dose (ppm) | % Efficacy | Synergism (Colby) |
|---|---|---|---|
| Compound 1 | 4.1 | 28 | — |
| Fenhexamid | 37 | 35 | — |
| Compound 1 + fenhexamid (Ratio 1:9) | 4.1 + 37 | 74 | +21 |

According to the Colby method, a synergistic effect of the mixtures tested has been observed.

Example 12: Efficacy Against *Mycosphaerella graminicola* of a Mixture Containing N-{2-[3-chloro-5-(trifluoromethyl)-2-pyridinyl]ethyl}-2-trifluoromethylbenzamide (Compound 1) and prochloraz The formulated compounds are diluted with water to obtain the desired active material concentration Wheat plants (Scipion variety), sown on a 50/50 peat soil-pozzolana substrate in starter cups and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Mycosphaerella graminicola* spores (500 000 spores per ml). The spores are collected from a 7-day-old culture. The contaminated wheat plants are incubated for 72 hours at 18° C. and at 100% relative humidity, and then for 21 to 28 days at 90% relative humidity.

Grading (% of efficacy) is carried out 21 to 28 days after the contamination, in comparison with the control plants.

The following table summarises the results obtained when tested compound 1 and prochloraz alone and in a 1:4 weight ratio mixture.

|  | Dose (g/ha) | % Efficacy | Synergism (Colby) |
|---|---|---|---|
| Compound 1 | 62.5 | 77 | — |
| Prochloraz | 250 | 54 | — |
| Compound 1 + Prochloraz (Ratio 1/4) | 62.5 + 250 | 98 | +9 |

According to the Colby method, a synergistic effect of the mixtures tested has been observed.

Example 13: Efficacy Against *Botrytis cinerea* of a Mixture Containing N-{2-[3-chloro-5-(trifluoromethyl)-2-pyridinyl]ethyl}-2-trifluoromethylbenzamide (Compound 1) and fenpropimorph The formulated compounds are diluted with water to obtain the desired active material concentration.

Gherkin plants (Petit vert de Paris variety) in starter cups, sown on a 50/50 peat soil-pozzolana substrate and grown at 18-20° C., are treated at the cotyledon Z11 stage by spraying with the aqueous suspension described above. Plants, used as controls, are treated with an aqueous solution not containing the active material.

After 24 hours, the plants are contaminated by depositing drops of an aqueous suspension of *Botrytis cinerea* spores (150,000 spores per ml) on upper surface of the leaves. The spores are collected from a 15-day-old culture and are suspended in a nutrient solution composed of:
20 g/L of gelatine
50 g/L of cane sugar
2 g/L of NH4NO3
1 g/L of KH2PO4

The contaminated gherkin plants are settled for 5/7 days in a climatic room at 15-11° C. (day/night) and at 80% relative humidity. Grading of efficacy is carried out 5 to 7 days after the contamination, in comparison with the control plants.

The following table summarises the results obtained when tested compound 1 and fenpropimorph alone and in 1:2 weight ratio mixture.

|  | Dose (g/ha) | % Efficacy | Synergism (Colby) |
|---|---|---|---|
| Compound 1 | 31.2 | 20 | — |
|  | 62.5 | 30 | — |
| Fenpropimorph | 62.5 | 10 | — |
|  | 125 | 30 | — |
| Compound 1 + fenpropimorph (Ratio 1:2) | 31.2 + 62.5 | 60 | +32 |
|  | 62.5 + 125 | 80 | +29 |

According to the Colby method, a synergistic effect of the mixtures tested has been observed.

Example 14: Efficacy Against *Erysiphe graminis* f. sp. *graminis* of a Mixture Containing N-{2-[3-chloro-5-(trifluoromethyl)-2-pyridinyl]ethyl}-2-trifluoromethylbenzamide (Compound 1) and spiroxamine The formulated compounds are diluted with water to obtain the desired active material concentration Wheat plants (Audace variety) in starter cups, sown on 50/50 peat soil-pozzolana substrate and grown at 12° C., are treated at the 1-leaf stage (10 cm tall) by spraying with the aqueous suspension described above.

Plants, used as controls, are treated with an aqueous solution not containing the active material.

After 24 hours, the plants are contaminated by dusting them with *Erysiphe graminis* f. sp. *tritici* spores, the dusting being carried out using diseased plants.

Grading is carried out 7 to 14 days after the contamination, in comparison with the control plants.

The following table summarises the results obtained when tested compound 1 and spiroxamine alone and in a 4:1 weight ratio mixture.

|  | Dose (g/ha) | % Efficacy | Synergism (Colby) |
|---|---|---|---|
| Compound 1 | 500 | 44 | — |
| Spiroxamine | 125 | 0 | — |
| Compound 1 + spiroxamine (Ratio 4:1) | 500 + 125 | 72 | +28 |

According to the Colby method, a synergistic effect of the mixtures tested has been observed.

Example 15: Efficacy Against *Botrytis cinerea* of a Mixture Containing N-{2-[3-chloro-5-(trifluoromethyl)-2-pyridinyl]ethyl}-2-trifluoromethylbenzamide (Compound 1) and triforine The formulated compounds are diluted with water to obtain the desired active material concentration.

Gherkin plants (Petit vert de Paris variety) in starter cups, sown on a 50/50 peat soil-pozzolana substrate and grown at 18-20° C., are treated at the cotyledon Z11 stage by spraying with the aqueous suspension described above. Plants, used as controls, are treated with an aqueous solution not containing the active material.

After 24 hours, the plants are contaminated by depositing drops of an aqueous suspension of *Botrytis cinerea* spores (150,000 spores per ml) on upper surface of the leaves. The spores are collected from a 15-day-old culture and are suspended in a nutrient solution composed of:
20 g/L of gelatine
50 g/L of cane sugar
2 g/L of NH4NO3
1 g/L of KH2PO4

The contaminated gherkin plants are settled for 5/7 days in a climatic room at 15-11° C. (day/night) and at 80% relative humidity. Grading (% of efficacy) is carried out 5 to 7 days after the contamination, in comparison with the control plants.

The following table summarises the results obtained when tested compound 1 and triforine alone and in different weight ratio mixtures.

|  | Dose (ppm) | % Efficacy | Synergism (Colby) |
| --- | --- | --- | --- |
| Compound 1 | 37 | 50 | — |
| Triforine | 37 | 0 | — |
|  | 111 | 15 | — |
| Compound 1 + triforine (Ratio 1:1) | 37 + 37 | 65 | +15 |
| Compound 1 + triforine (Ratio 1:3) | 37 + 111 | 70 | +13 |

According to the Colby method, a synergistic effect of the mixtures tested has been observed.

Example 16: Efficacy Against *Botrytis cinerea* of a Mixture Containing N-{2-[3-chloro-5-(trifluoromethyl)-2-pyridinyl]ethyl}-2-trifluoromethylbenzamide (Compound 1) and bitertanol The formulated compounds are diluted with water to obtain the desired active material concentration.

Gherkin plants (Petit vert de Paris variety) in starter cups, sown on a 50/50 peat soil-pozzolana substrate and grown at 18-20° C., are treated at the cotyledon Z11 stage by spraying with the aqueous suspension described above. Plants, used as controls, are treated with an aqueous solution not containing the active material.

After 24 hours, the plants are contaminated by depositing drops of an aqueous suspension of *Botrytis cinerea* spores (150,000 spores per ml) on upper surface of the leaves. The spores are collected from a 15-day-old culture and are suspended in a nutrient solution composed of:

20 g/L of gelatine 50 g/L of cane sugar 2 g/L of NH4NO3

1 g/L of KH2PO4

The contaminated gherkin plants are settled for 5/7 days in a climatic room at 15-11° C. (day/night) and at 80% relative humidity. Grading (% of efficacy) is carried out 5 to 7 days after the contamination, in comparison with the control plants.

The following table summarises the results obtained when tested compound 1 and bitertanol alone and in a 1:9 weight ratio mixture.

|  | Dose (ppm) | % Efficacy | Synergism (Colby) |
| --- | --- | --- | --- |
| Compound 1 | 12.3 | 5 | — |
| Bitertanol | 333 | 0 | — |
| Compound 1 + bitertanol (Ratio 1:9) | 12.3 + 333 | 95 | +90 |

According to the Colby method, a synergistic effect of the mixture tested has been observed.

Example 17: Efficacy Against *Erysiphe graminis* f. sp. *graminis* of a Mixture Containing N-{2-[3-chloro-5-(trifluoromethyl)-2-pyridinyl]ethyl}-2-trifluoromethylbenzamide (Compound 1), spiroxamine and prothioconazole The formulated compounds (Compound 1 and a mix of spiroxamine (300 g/l) and prothioconazole (160 g/l) are diluted with water to obtain the desired active material concentration Wheat plants (Audace variety) in starter cups, sown on 50/50 peat soil-pozzolana substrate and grown at 12° C., are treated at the 1-leaf stage (10 cm tall) by spraying with the aqueous suspension described above.

Plants, used as controls, are treated with an aqueous solution not containing the active material.

After 24 hours, the plants are contaminated by dusting them with *Erysiphe graminis* f. sp. *tritici* spores, the dusting being carried out using diseased plants.

Grading is carried out 7 to 14 days after the contamination, in comparison with the control plants.

The following table summarises the results obtained when tested compound 1 and the mix of spiroxamine and prothioconazole alone and in a 8:1 weight ratio mixture.

|  | Dose (g/ha) | % Efficacy | Synergism (Colby) |
| --- | --- | --- | --- |
| Compound 1 | 125 | 0 | — |
| Spiroxamine + prothioconazole | 15.6 | 45 | — |
| Compound 1 + spiroxamine + prothioconazole (Ratio 8:1) | 125 + 15.6 | 95 | +50 |

According to the Colby method, a synergistic effect of the mixtures tested has been observed.

The invention claimed is:

1. A composition comprising:
   (a) N-{2-[3-chloro-5-(trifluoromethyl)-2-pyridinyl]ethyl}-2-trifluoromethylbenzamide or its N-oxide from the pyridine moiety; and
   (b) a compound selected from the group consisting of fenhexamid and fenpropimorph;
   In an (a)/(b) weight ratio of from 0.01 to 20.

2. The composition of claim 1, wherein the (b) compound is fenhexamid.

3. The composition of claim 1, wherein the (b) compound is fenpropimorph.

4. The composition of claim 2 wherein the (a)/(b) weight ratio is 1.

5. The composition of claim 1 further comprising an agriculturally acceptable support, carrier, filler and/or surfactant.

6. The composition of claim 1, wherein (a) and (b) are the only two active components present.

7. The composition of claim 1, wherein the (a)/(b) weight ratio is from 0.05 to 10.

8. The composition of claim 1, wherein the (a)/(b) weight ratio is from 0.1 to 5.

9. A method for preventively or curatively controlling phytopathogenic fungi of crops comprising applying an effective and non-phytotoxic amount of the composition of claim 1 to the seed, the plant and/or to the fruit of the plant or to the soil in which the plant is growing or in which it is desired to grow.

10. A method for preventively or curatively controlling phytopathogenic fungi of crops comprising applying an effective and non-phytotoxic amount of the composition of claim 5 to the seed, the plant and/or to the fruit of the plant or to the soil in which the plant is growing or in which it is desired to grow.

* * * * *